United States Patent [19]
Johnson

[11] Patent Number: 4,515,430
[45] Date of Patent: May 7, 1985

[54] INTEGRATED OPTICAL TRANSDUCERS

[75] Inventor: Leonard M. Johnson, Cambridge, Mass.

[73] Assignee: Massachusetts Institute of Technology, Cambridge, Mass.

[21] Appl. No.: 502,348

[22] Filed: Jun. 10, 1983

Related U.S. Application Data

[63] Continuation of Ser. No. 187,041, Sep. 15, 1980, abandoned.

[51] Int. Cl.³ ............................................. G02B 5/174
[52] U.S. Cl. ............................ 350/96.13; 350/96.12; 356/345
[58] Field of Search ............... 350/96.12, 96.13, 96.14, 350/96.29, 96.15; 356/345, 349, 350, 351

[56] References Cited

U.S. PATENT DOCUMENTS

| | | | |
|---|---|---|---|
| 3,819,250 | 6/1974 | Kibler | 350/96.29 |
| 3,920,314 | 11/1975 | Yajima | 350/96.12 |
| 3,957,340 | 5/1976 | Giallorenzi | 350/96.14 |
| 4,070,094 | 1/1978 | Martin | 350/96.14 |
| 4,128,300 | 12/1978 | Stotts et al. | 350/96.14 |
| 4,147,979 | 4/1979 | Baues et al. | 324/244 |
| 4,266,850 | 5/1981 | Burns | 350/96.14 |
| 4,288,785 | 9/1981 | Papuchon et al. | 350/96.14 X |
| 4,300,814 | 11/1981 | Carenco | 350/96.12 |
| 4,340,272 | 7/1982 | Papuchon et al. | 350/96.14 |

OTHER PUBLICATIONS

Yajima, "Dielectric Branching Waveguide," *Appl. Phys. Lett.*, vol. 22, No. 12, 15 Jun. 1973, pp. 647–649.
Martin, "A New Waveguide Switch/Modulator . . .", *Appl. Phys. Lett.*, vol. 26, No. 10, 15 May 1975, pp. 562–564.
Glatzel et al, "Temperature Measurement Technique . . .", *IBM Tech. Discl. Bull.*, vol. 20, No. 11A, Apr. 1978, pp. 4571–4572.
Taylor et al, "Electro-Optic Analog-to-Digital Conversion . . .", *Appl. Phys. Lett.*, vol. 32, No. 9, 1 May 1978, pp. 559–561.
Ranganath et al, "Ti-Diffused LiNBO₃ . . . Modulators . . .", *IEEE J. Quantum Electronics*, vol. QE-13, No. 4, Apr. 1977, pp. 290–295.
Taylor, "An Optical A-to-D Converter . . .", *IEEE J. Quantum Electronics*, vol. QE-15, No. 4, Apr. 1979, pp. 210–216.
Bulmer et al, "Linear Interferometric Waveguide Modulator . . .", *Optics Letters*, vol. 5, No. 5, May 1980, pp. 176–178.
Leonberger, "High Speed . . . Interferometric Waveguide Modulators", *Optics Letters*, vol. 5, No. 7, Jul. 1980, pp. 312–314.
Leonberger, "High-Speed Electro-Optical . . . Devices", *SPIE* vol. 218, 1980, pp. 41–46.

*Primary Examiner*—John Lee
*Attorney, Agent, or Firm*—Arthur A. Smith, Jr.; Thomas J. Engellenner

[57] ABSTRACT

An integrated optical transducer includes a single mode input optical waveguide, two single mode optical waveguide branches having different physical lengths, and a single mode output optical waveguide. When used as a transducer, the optical path lengths of the waveguide branches are dependent on the physical quantity measured. A plurality of such transducer elements may be used jointly to provide a binary output of high sensitivity and wide range of measurement. The waveguide element may also be used as an optical pulse source.

20 Claims, 5 Drawing Figures

FIG. 3
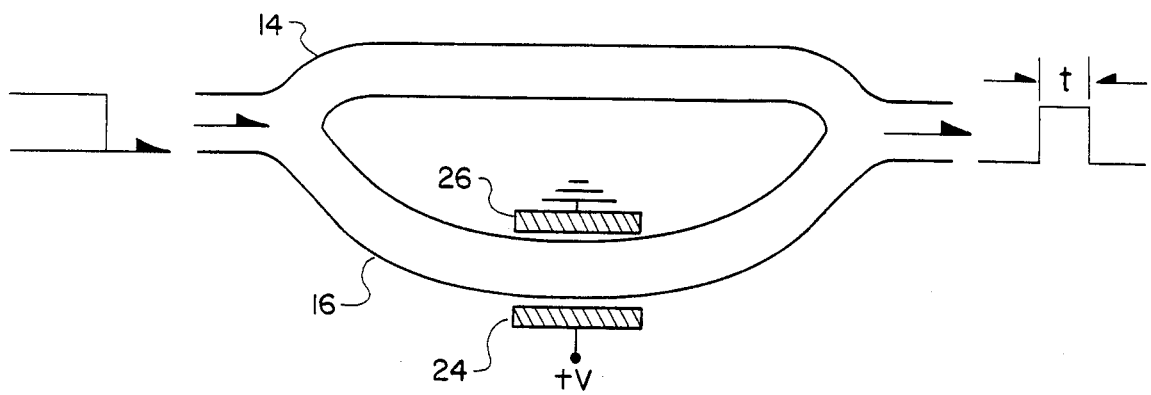
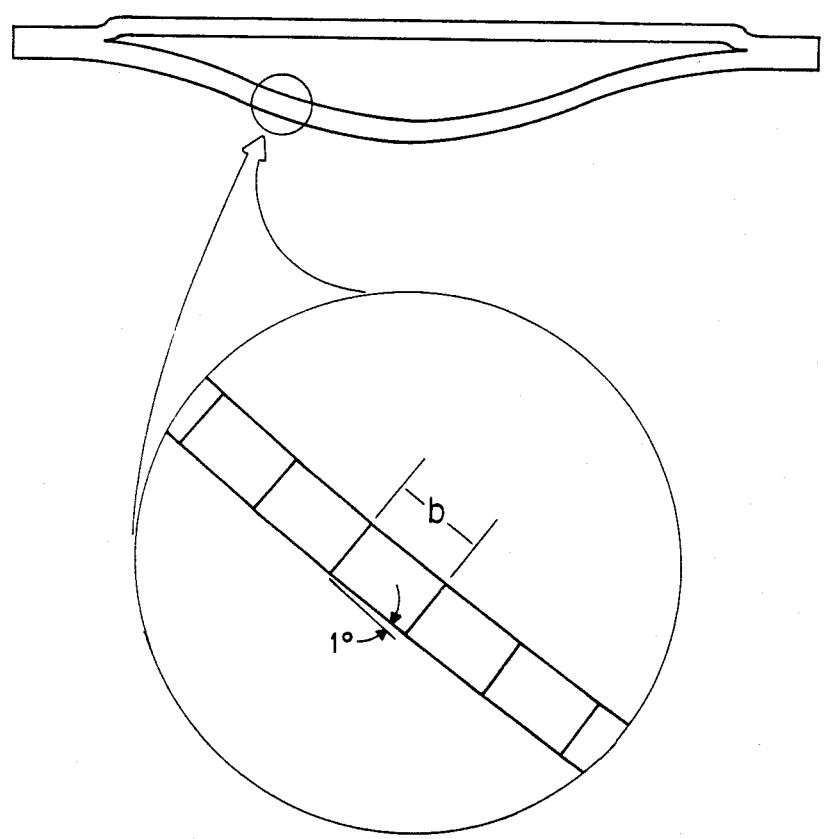
FIG. 4

INTEGRATED OPTICAL TRANSDUCERS

The Government has rights in this invention pursuant to M.I.T. Sub-Contract #E-21-A44, under Prime Navy Contract Number N61339-75-C-0122 awarded to the Georgia Institute of Technology.

This application is a continuation of application Ser. No. 187,041, filed Sept. 15,1980 (now abandoned).

DESCRIPTION

1. Technical Field

This invention relates to optical transducers and more particularly to a modified integrated optical Mach-Zehnder interferometer.

2. Background

In recent years there has been considerable progress in integrated optics technology. Optical devices such as modulators, switches and multiplexers have been successfully fabricated on single substrates of both dielectrics and semiconductors. These devices are rugged, compact and relatively easy to construct. They are also compatible with optical fibers, semiconductor lasers and photodiodes. One such optical device is the Mach-Zehnder interferometeric modulator. In that device, an optical signal in an input optical waveguide is divided into two branches of equal lengths. The signals from the two branches are then recombined in a single-mode output waveguide. By electro-optically varying the index of refraction of one or both of those branches, the relative phase of the light at the end of each branch can be varied. The interference of those two recombined signals results in an output intensity which is dependent on the index of refraction of the controlled branch. In order to shift the operating point of the modulator, very small differences in branch physical length of less than one wavelength have been provided.

An object of the present invention is to provide a transducer based on integrated optics technology which has the advantages noted above for other integrated optical devices. Such a transducer also has the advantages of electrical noise immunity and high sensitivity.

A particular object of this invention is to provide a temperature sensitive optical transducer.

DISCLOSURE OF THE INVENTION

An integrated optical device includes an input optical waveguide, at least two waveguide branches and an output waveguide into which the branches reconverge. The optical path length of one of those branches is substantially greater than that of the other branch. Any physical quantity which affects the index of refraction of the waveguide branches or the length of those branches affects the modal power distribution of light in the output waveguide and thus provides an indication of the physical quantity.

Preferably, each of the waveguides is a single mode waveguide. One or both of the waveguide branches may be electro-optically controlled.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 3 is a plan view of an electro-optically controlled emodiment of the invention;

FIG. 4 illustrates the actual fabrication of a transducer embodying this invention.

DESCRIPTION OF PREFERRED EMBODIMENTS

In general, electromagnetic energy is transmitted through waveguides in a finite number of propagation modes. The propagation modes are classified as a TE mode where there is an electric field component only in the transverse direction and as a TM mode where there is a magnetic field component only in the transverse direction. Depending on the dimensions of the waveguide, TE mode waves, for example, can be transmitted as one or more modes distinguished by the number of peaks in the distribution of the electric field across the waveguide. For example, a single mode waveguide only permits the transmission of first order modes in which the electric field distribution has a single peak across the waveguide. Double mode waveguides permit transmission of both the first order mode and the second order mode in which there are two peaks in the electric field across the waveguide.

Figure 1:
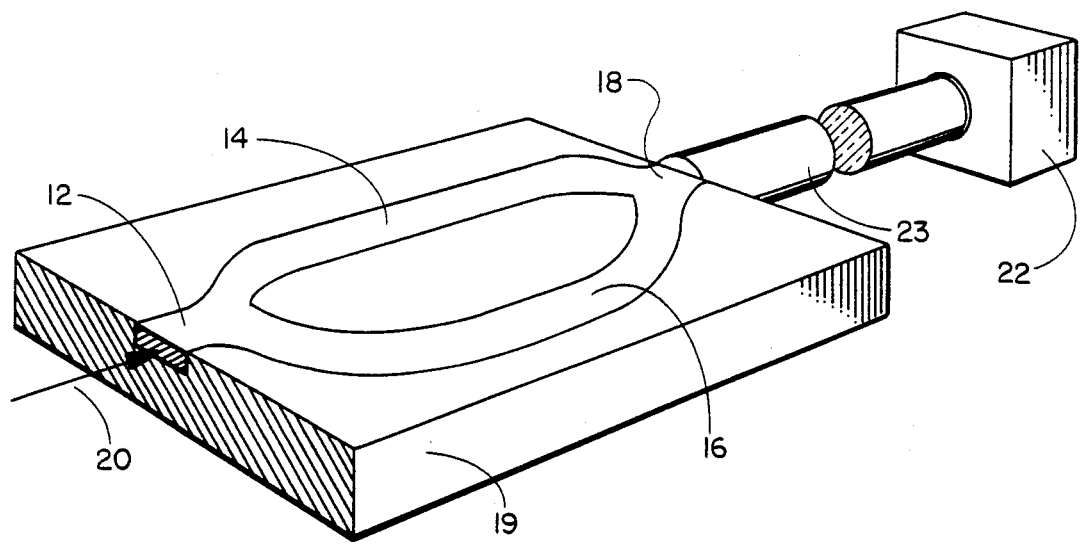
FIG. 1 is a perspective view of a transducer embodying this invention.

FIG. 1 shows a transducer embodying this invention. The transducer includes an integral input single-mode waveguide 12, two single-mode waveguide branches 14 and 16 and a single-mode output waveguide 18 in a substrate 19. Light emitted from a coherent light source 20 passes through the input waveguide 12 and is split into the two branches 14 and 16. The light signals which diverge in the paths 14 and 16 reconverge in the output waveguide 18; but due to the difference in optical path lengths of the branches 14 and 16, the two signals are shifted in phase relative to each other. Depending on the phase relationship of the output signals, they either constructively or destructively interfere. If the two signals are exactly in phase the light detected by light detector 22 through optical fibers 23 is at a maximum. If the two signals are 180° out of phase no light will be detected by detector 22.

The optical path length of either of the branches 14 or 16 can be defined as:

$$\phi = 2\pi/\lambda nL \qquad (1)$$

where $\lambda$ is the wavelength of the optical signal, n is the effective index of refraction of the waveguide and L is the physical length of the waveguide. The power of the light in the output waveguide $P_o$ can be related to the power at the input waveguide 12 $P_i$ by the following equation:

$$P_o = P_i/2[1 + \cos(\phi_1 - \phi_2)] \qquad (2)$$

where $\phi_1$ and $\phi_2$ are the optical path lengths of the long and short branches 16 and 14, respectively.

It can be seen from equations 1 and 2 that, because the lengths L1 and L2 of the respective branches are unequal, even where the index of refraction of the two branches is the same any change in that index of refraction will affect the optical path lengths of each branch to a different degree and will thus change the value $(\phi_1 - \phi_2)$. With changes in $(\phi_1 - \phi_1)$ from odd multiples of $\pi$ to even multiples of $\pi$, the output power $P_o$ will change from zero to the maximum power $P_i$. If the index of refraction of the waveguides is temperature dependent, changes in the index of refraction with temperature will result in a change in the output signal indicative of temperature.

The sensitivity of the transducer to the particular physical quantity to be measured is determined by the difference in lengths $L_1 - L_2$. For example, to provide for a maximum change in power at the output of the transducer over a temperature range $\Delta T_\pi$, the change in $(\phi_1 - \phi_2)$ over that temperature range must equal $\pi$. Thus, one can determine the difference in physical length $L_1 - L_2$ by setting the derivative of $(\phi_1 - \phi_2)$ with respect to temperature at $\pi/\Delta T_\pi$. From equation 1, where the index of refraction is the same for each branch, $$\phi_1 - \phi_2 = 2\pi n/\lambda (L_1 - L_2) \tag{3}$$

Assuming that the change in length of the branches is minimal relative to the change in the index of refraction with temperature, $$\frac{d(\phi_1 - \phi_2)}{dT} = \frac{2\pi}{\lambda}(L_1 - L_2)\frac{dn}{dT} = \frac{\pi}{\Delta T_\pi} \tag{4}$$

$$(L_1 - L_2) = \frac{\lambda}{2\Delta T_\pi}\left(\frac{dn}{dT}\right)^{-1} \tag{5}$$

Thus, with an optical signal having a wavelength of $1\mu$, and an index of refraction which changes with temperature at a rate of $10^{-4}/°C$., a maximum change in intensity at the output of the transducer can be obtained over a range of 1° C. if the difference in lengths of the two branches is 5 millimeters. Because the change in the index of refraction with temperature is very small, the difference in lengths between the two branches must be many times greater than the wavelength of the light, and in this case, must be three orders of magnitude larger than the wavelength.

In actuality, the coefficient of linear expansion of the waveguide branches are of the same order of magnitude as the rate of change of the index of refraction with temperature. Thus, one must consider that coefficient of linear expansion, and the derivative of $(\phi_1 - \phi_2)$ with respect to temperature in equation 4 becomes:

$$\frac{d(\phi_1 - \phi_2)}{dT} = \frac{2\pi}{\lambda}\left[n\frac{d(L_1 - L_2)}{dT} + (L_1 - L_2)\frac{dn}{dT}\right] \tag{6}$$

For measuring small temperature fluctuations $\Delta T$ about $T_o$, the optimum operating points $(\phi_1 - \phi_2)/T_o$ are equal to $m\pi/2 (m = 1, 3, 5, \ldots)$. The optical output power is then related to the temperature fluctuation $\Delta T$ by the relation:

$$P_o = \frac{P_i}{2}(1 + S\Delta T) \tag{7}$$

where $$s = \frac{d(\phi_1 - \phi_2)}{dT}\bigg|_{T_o} \tag{8}$$

Thus far, the transducer of FIG. 1 has been described as a temperature sensing transducer. The transducer may also be used to sense any other parameter on which either the index of refraction or the length of the branch waveguides are dependent. For example, the transducer may also be used to measure pressure, strain, electric or magnetic fields, electromagnetic radiation or chemical activity.

Because the transducer has a sinusoidal output, if a transducer has been designed to provide a maximum intensity deviation over a small range of the measured temperature, the transducer output oscillates through a wide temperature range. For example, if the transducer is designed for a maximum intensity deviation over a one degree temperature change, the same output sweep is repeated ten times through a ten degree temperature change. Thus, to provide the high sensitivity of such a short range transducer over a wider measurement range, a bank of transducers, each designed for a different temperature range, may be provided in the single substrate.

Figure 5:
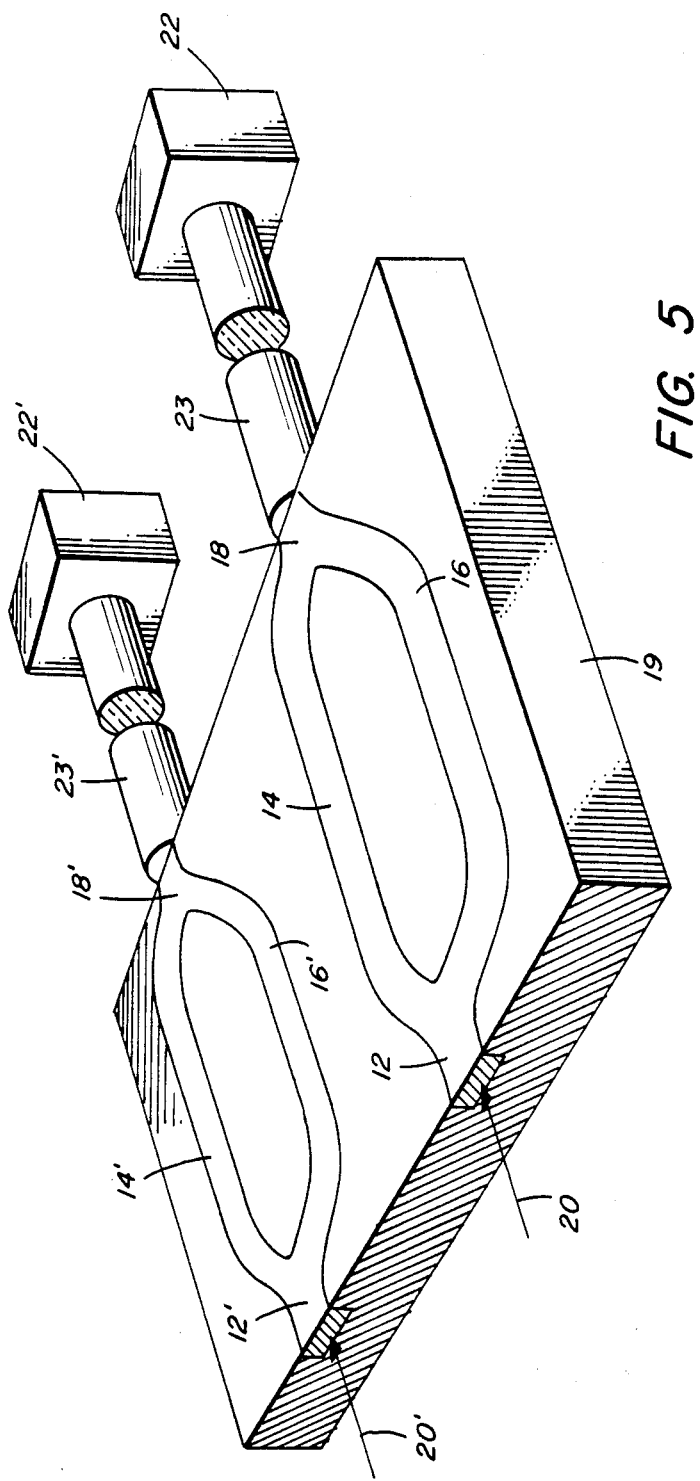
FIG. 5 is a perspective view of an embodiment of the invention in which a plurality of transducer elements are disposed upon a common substrate.

FIG. 5 illustrates such a bank of transducer elements. Substrate 19 carries a first transducer element including input waveguide 12, unequal waveguide branches 14 and 16, and output waveguide 18; and a second transducer element including input waveguide 12', unequal waveguide branches 14' and 16', and output waveguide 18'. Light waves emitted from a first source 20 and a second source 20', pass through the first and second transducer elements, respectively, and are transmitted via optical fibers 23 and 23' to the respective detectors 22 and 22'. The transducer elements are designed to provide maximum intensity deviations over different temperature ranges. Although a bank of two transducer elements is illustrated, larger banks also can be constructed.

This use of a bank of transducer elements in a single transducer is ideally suited for a binary output such as a Gray code. The output from the most sensitive transducer could be digitized to provide any degree of resolution. Other transducers would demonstrate a systematic variation in path length difference to cover temperature ranges which are weighted according to the binary code. For example, a first transducer would provide the high resolution signal through a one degree range. The second transducer might cover a two degree range, a third transducer might cover a four degree range and the next transducer would be designed for an eight degree range. Together, those four transducers could provide a high resolution output over an eight degree temprature range.

Figure 2:
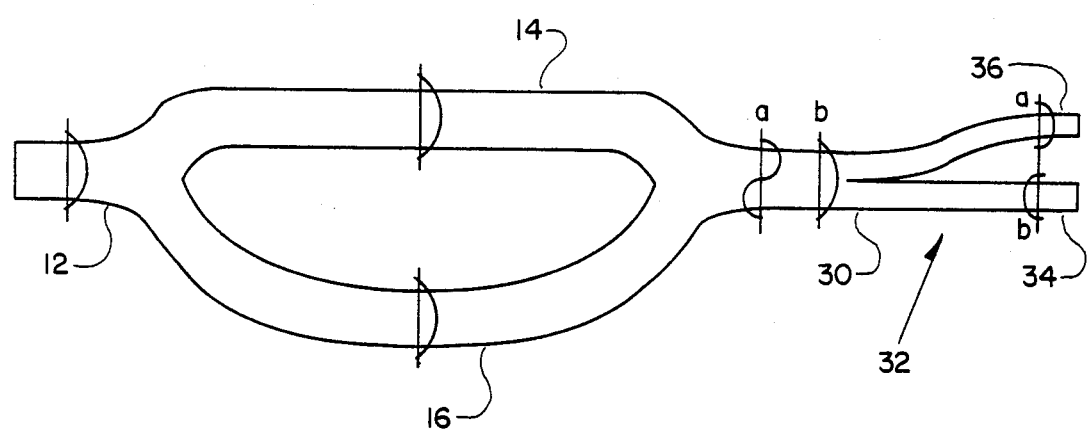
FIG. 2 illustrates an embodiment of the invention in which the waveguides are not all single mode waveguides.

The above-described embodiment made use of only single mode waveguides. Double and even higher mode waveguides may also be used. As an example, FIG. 2 shows a transducer which includes a single mode input, single mode branches and a double mode output waveguide 30. The double mode output waveguide is split into a single mode branch filter 32 which splits the first and second outputs into respective waveguides 34 and 36. Such a filter is shown in U.S. Pat. No. 3,920,314 to Yajima. The power of the signal in either waveguide can be detected to provide an indication of temperature. Thus, it can be seen that, although the single mode embodiment is preferred for its inherent filtering capabilities, the real parameter of interest in the output waveguide is the modal power distribution.

A further embodiment of the invention is shown in FIG. 3. That device includes electrodes 24 and 26 associated with one branch of the transducer, in this case the longer branch 16. Those electrodes may be used to electro-optically control the index of refraction of the branch and thus control the optical path length. Thus the device can be used for amplitude modulation and the like. Further, as shown, when a stepped input is provided to the device at the input waveguide, a pulsed output may be obtained. With the branch 16 electro-optically biased to yield $(\phi_1-\phi_2)$ equal to $m\pi (m=1, 3, 5 \ldots)$, the optical output resulting from a fast rise time step function input signal as shown to the left of the figure is an ultrashort rectangular pulse of duration $t=n(L_1-L_2)/c$ where c is the speed of light. The output pulse width t corresponds to the difference in optical transit time between the two branches of the device and that time is roughly one picosecond for path length difference of 0.1 millimeter. The output pulse width is limited only by the rise time of the input optical signal.

There are several primary criteria for choosing the material and fabrication technique for the integrated interferometric temperature sensor described above. To fabricate low attenuation, single mode waveguides the material must be of high quality and the fabrication process must allow the careful control of waveguide dimensions. To minimize the waveguide bending losses there must also be tight confinement of the optical field within the guiding region. This can be achieved in a material system where large variations in index of refraction can be introduced. The material parameters must also be temperature sensitive in order to achieve measureable temperature dependent variations in optical output power.

Titanium-diffused lithium niobate (Ti:LiNbO$_3$) is currently the best material system available in terms of the above criteria. Waveguides are formed just beneath the surface of a LiNbO$_3$ substrate. Guiding occurs due to refractive index increases proportional to the diffused Ti concentration. Single mode waveguides with losses of about 1 db/cm have been fabricated by depositing $3\mu$ wide, 300Å thick titanium stripes on a lithium niobate substrate using conventional photolithographic techniques and diffusing the titanium at 980° C for 6 hours. Following the diffusion, the end faces of the sample are polished to allow coupling of the light into and out of the waveguides. The resulting waveguides are approximately $4\mu$ wide by $3\mu$ deep with a maximum index increase of $2\times10^{-2}$ on the surface of the LiNbO$_3$ at the center of the guides.

The temperature sensitivity of a Ti-diffused LiNbO$_3$ transducer can be calculated from equation 7 using the parameters $dn/dT=6\times10^{-5}$ °C.$^{-1}$ and $1/L dL/dT=1.5\times10^{-5}$ °C.$^{-1}$, yielding $$\frac{d(\phi_1-\phi_2)}{dT} = s = \frac{2\pi}{\lambda}(L_1-L_2)(9.5\times10^{-5})°C.^{-1} \quad (9)$$

$$= 9.4\times10^{-2} °C.^{-1}$$

for $\lambda=6328Å$ and $L_1-L_2=0.1$ mm.

If the input intensity is $50\mu$ watts and a silicon photodiode having a photodiode quantum efficiency of 0.5 and a detection bandwidth of 10 hz is used to measure the optical output, the minimum detectable power is shot noise limited with a signal to noise ratio (SNR) of 100 for temperature fluctuation of $\Delta T = 10^{-4}$° C.

The most difficult problem in fabricating the unequal length interferometer is keeping the waveguide bend losses at an acceptable level. To acheive a path length difference of 0.1 mm with a device length of 1 cm, a bend radius of 1 cm is required in the long arm of the interferometer. This results in a maximum off axis bend of 15°. State-of-the-art photomask pattern generators do not allow the fabrication of perfectly circular waveguide bends at micron dimensions. Circular bends can only be approximated by a series of straight segments connected by abrupt bends. Abrupt bends of 1-2° are typically found in waveguide devices with losses of about 1 db for 1° bends and 3 db for 2° bends. Using these values the bending loss in the long arm of the interferometer would be about 60 db for 60 straight sections connected by 1° bends. This loss is considered to be too high for a useful device.

Bending losses have been dramatically reduced by taking advantage of a coupling effect between successive abrupt bends. Henry Taylor proposed in a theoretical analysis that the loss through a waveguide structure of successive bends could be a strong oscillatory function of the distance between each bend. Henry F. Taylor, "Power Loss at Directional Change In Dielectric Waveguides", *Applied Optics*, Vol. 13, pp. 642–647 (1974).

An interferometer transducer with $L_1-L_2=0.1$ mm and utilizing a low loss 60-section bend structure for the long branch 16 is shown in FIG. 4. The short branch 14 includes two two-section bends. The interconnection length for each is $180\mu$. The transmission of the 60-section bend is only 6 db below a straight waveguide comparable length. This measured loss is far below the 60 db loss predicted for a series of 60 isolated 1° bends.

It should be recognized that other types of waveguides such as a rib waveguide may reduce the losses even further.

While the invention has been particulary shown and described with reference to preferred embodiments thereof, it will be understood by those skilled in the art that various changes in form and details may be made therein without departing from the spirit and scope of the invention as defined by the appended claims.

I claim:

1. An optical transducer for measuring a physical quantity comprising:
   an input optical waveguide for transmitting an optical signal;
   at least two optical waveguide branches having different optical path lengths and in which said optical signal diverges, the difference in optical path lengths being many times greater that the wavelength of the optical signal and to a substantial degree, a function of the difference in physical lengths and the optical path length of each branch being a function of said physical quantity;
   an output optical waveguide into which the optical signals reconverge; and
   means for providing an indication of the modal power distribution in the output waveguide as an indication of said physical quantity.

2. An optical transducer for measuring a physical quantity comprising:
   an input optical waveguide for transmitting an optical signal;
   at least two optical waveguide branches having different physical lengths and in which said optical signal diverges, the difference in physical lengths being many times greater than the wavelength of the optical signal and the optical path length of each branch being a function of said physical quantity; and
   an output optical waveguide into which the optical signals reconverge.

3. An optical transducer for measuring a physical quantity comprising:
   a single mode input optical waveguide for transmitting an optical signal;
   at least two single mode optical waveguide branches having different physical lengths and in which said optical signal diverges, the difference in physical lengths being many times greater than the wavelength of the optical signal and the optical path length of each branch being a function of said physical quantity;
   an output optical waveguide into which the optical signals reconverge; and
   means for providing an indication of the modal power distribution in the output optical waveguide as an indication of said physical quantity.

4. An optical transducer adapted for measuring a physical quantity comprising, in a common sub-strate:
   a single mode input optical waveguide for transmitting an optical signal;
   at least two single mode optical waveguide branches having different physical lengths and in which said optical signal diverges, the difference in physical lengths being many times greater than the wavelength of the optical signal and the optical path length of each branch being a function of said physical quantity; and
   a single mode output optical waveguide into which the optical signals reconverge.

5. An optical transducer as claimed in claim 1, 2, 3 or 4 wherein the physical quantity measured is temperature and the optical path length of each branch is a function of temperature.

6. An optical transducer as claimed in claim 5 wherein the indexes of refraction of the two optical waveguide branches are equal and are temperature dependent.

7. An optical transducer as claimed in claim 5 wherein both the index of refraction and the physical length of each optical waveguide branch are temperature dependent.

8. An optical transducer as claimed in claim 1, 2 3 or 4 further comprising electrodes for electo-optically controlling the optical path length of at least one of the optical waveguide branches.

9. An optical transducer as claimed in claim 1, 2 3 or 4 comprising, in a common substrate, a plurality of pairs of optical waveguide branches and a plurality of output optical waveguides, at least some of the length differences of optical waveguide branch pairs being different to provide output signals having differing sensitivities to the physical quantity.

10. An optical transducer as claimed in claim 9 wherein the path length differences of the pairs of optical waveguide branches provide binary weighted outputs.

11. An optical transducer as claimed in claim 2 or 4 further comprising means for providing an indication of the modal power distribution in the output optical waveguide as an indication of said physical quantity.

12. An optical waveguide interferometer comprising, in a common substrate:
   an input optical waveguide for transmitting an optical signal;
   at least two optical waveguide branches having different physical lengths and in which said optical signal diverges, the difference in physical lengths being many times greater than the wavelength of the optical signal; and
   an output optical waveguide into which the optical signals reconverge.

13. An optical interferometer as claimed in claim 12 further comprising electrodes for electro-optically controlling the optical path length of at least one of the optical waveguide branches.

14. An optical interferometer as claimed in claim 12 wherein each of said optical waveguides is a single mode waveguide.

15. A method of sensing a physical quantity comprising:
   providing an integrated optical transducer comprising, on a single substrate, at least two optical waveguide branches for transmitting an optical signal, the branches having different physical lengths and which diverge from a common input and reconverge into a common output, the difference in optical path lengths being many times greater that the wavelength of the optical signal;
   transmitting the optical signal through the optical waveguide branches from the common input while simultaneously subjecting both waveguide branches to a physical quantity which affects the optical path lengths of the branches; and
   monitoring the optical signal at the common output of the waveguide branches.

16. A method as claimed in claim 15 wherein the waveguide branches are single mode waveguides and the common output is a single mode waveguide, and the intensity of light in the output waveguide is detected.

17. A method as claimed in claim 15 including a plurality of transducer elements on a common substrate, those transducer elements having varying differences in branch lengths to provide different measurement ranges at different sensitivities.

18. A method as claimed in claim 17 wherein the branch length differences provide binary weighted outputs.

19. A method of generating a pulsed optical signal comprising:
   providing an optical interferometer having two optical waveguide branches of different physical lengths which diverge from a common input and reconverge to a common output, the difference in physical lengths of the branches being an odd multiple of $\pi$; and
   transmitting a stepped optical signal through the waveguide branches from the common input.

20. A method as claimed in claim 19 wherein the optical path length difference between the two waveguide branches is maintained by electro-optic control of at least one of the branches.

* * * * *